(12) United States Patent
Wang

(10) Patent No.: US 7,276,535 B1
(45) Date of Patent: Oct. 2, 2007

(54) INTRATESTICULAR INJECTION OF CHEMICAL STERILANT

(75) Inventor: Min Wang, Columbia, MO (US)

(73) Assignee: Technology Transfer, Inc., Columbia, MO (US)

( * ) Notice: Subject to any disclaimer, the term of this patent is extended or adjusted under 35 U.S.C. 154(b) by 347 days.

(21) Appl. No.: 10/413,423

(22) Filed: Apr. 14, 2003

(51) Int. Cl.
*A61K 33/30* (2006.01)

(52) U.S. Cl. ............... 514/494; 424/422; 424/643; 514/565; 514/578

(58) Field of Classification Search .............. None
See application file for complete search history.

(56) References Cited

U.S. PATENT DOCUMENTS

| | | | |
|---|---|---|---|
| 4,156,427 A | 5/1979 | Fahim | 128/215 |
| 4,191,746 A | 3/1980 | Talwar | 424/92 |
| 4,339,438 A | 7/1982 | Fahim | 424/145 |
| 4,720,507 A | 1/1988 | Wiebe | 514/738 |
| 4,937,234 A | 6/1990 | Fahim | 514/53 |
| 5,070,080 A | 12/1991 | Fahim | 514/53 |
| 5,164,181 A | 11/1992 | Silver et al. | 424/94.63 |
| 5,372,822 A | 12/1994 | Fahim | 424/643 |

OTHER PUBLICATIONS

Fahim et al Sterilization Of Dogs- , Contraception 47: 107-122,, 1993.*

* cited by examiner

*Primary Examiner*—Neil S. Levy
(74) *Attorney, Agent, or Firm*—Grace J. Fishel

(57) ABSTRACT

A low effective dose of a biologically acceptable chemical sterilant is injected into the dorsal cranial portion of a scrotal testis of a male animal for the purpose effecting sterilization of the animal. The injection of the chemical sterilant into the dorsal cranial portion has an effect on the epithelium of the tubuli recti, rete testis and ductus efferentes in addition to stopping spermatogenesis in the seminiferous tubules.

3 Claims, 2 Drawing Sheets

INTRATESTICULAR INJECTION OF CHEMICAL STERILANT

BACKGROUND OF THE INVENTION

1. Field of the Invention

The present invention relates to a method of inhibiting spermatogenesis by injecting a chemical sterilant in a manner that promotes its effectiveness so that a lower dose is required for sterilization of an animal.

2. Brief Description of the Prior Art

Sterilization of male animals to limit reproduction in pets and livestock is usually effected by surgical castration. Surgery requires skilled personnel, a surgical suite with associated equipment and there are risks (e.g., anesthesia, infection and hemorrhage). A more humane and less costly method has been sought.

Many compounds have been explored for the purpose of arresting spermatogenesis chemically. Hormonal methods have been proposed but a method wherein the sterilant is injected into the testes is preferred because it exposes only the sperm producing tissue to the compound, thus avoiding direct distribution of foreign chemicals to non-reproductive tissues in the body. An injection into the testis also requires less skill than surgery to perform, opening the possibility that the procedure can also be practiced in developing and third world nations.

Various chemical agents have been injected into the testis for the purpose of interfering with the production of sperm in the seminiferous tubules. Many effective chemicals have been found too harsh to be used practically. An effective and biologically acceptable chemical sterilant was described in U.S. Pat. Nos. 4,937,234 and 5,070,080 to Fahim. In the '080 patent, the chemical sterilant was injected into the midline of the testis along the side or at the bottom of the testis. Depending upon the dose administered, spermatogenesis in the seminiferous tubules was completely stopped, effecting sterilization of the animal. It is preferred to administer the lowest possible effective amount but this gives rise to a chance that some portion of the testis will be left intact. If this occurs there is a possibility that a few sperm may reach the head of the epididymis. In view of the above, there is a need for a method of injecting the chemical sterilant described in U.S. Pat. Nos. 4,937,234 and 5,070,080 into a testis in a manner that the transport of any sperm is thwarted.

BRIEF SUMMARY OF THE INVENTION

In view of the above, it is an object of the present invention to provide a method for injecting a chemical sterilant into a testis in a manner that minimizes the dose necessary to effect sterilization. Other objects and features of the invention will be in part apparent and in part pointed out hereinafter.

In accordance with the invention, a low effective dose of a biologically acceptable chemical sterilant as described in U.S. Pat. Nos. 4,937,234 and 5,070,080 is injected into the dorsal cranial portion of a testis beside the epididymis. The injection of the chemical sterilant into the dorsal cranial portion has an effect on the epithelium of the tubuli recti, rete testis and ductus efferentes in addition to stopping spermatogenesis in the seminiferous tubules. If some of the seminiferous tubules in a portion of the testis remain intact, any sperm produced must pass through the above-mentioned transportation system to reach the epididymis. By affecting the epithelium of the tubuli recti, rete testis or ductus efferentes, the tubes may not add and remove fluids as is required for the successful development or maintenance of the sperm and there may be no cilia to sweep them along. Hence even if some portion of the testis remains intact, no viable sperm reach the epididymis and sterilization is complete.

The invention summarized above comprises the method hereinafter described, the scope of the invention being indicated by the subjoined claims.

DETAILED DESCRIPTION OF THE INVENTION

Testicular Structure and Function

Figure 1:
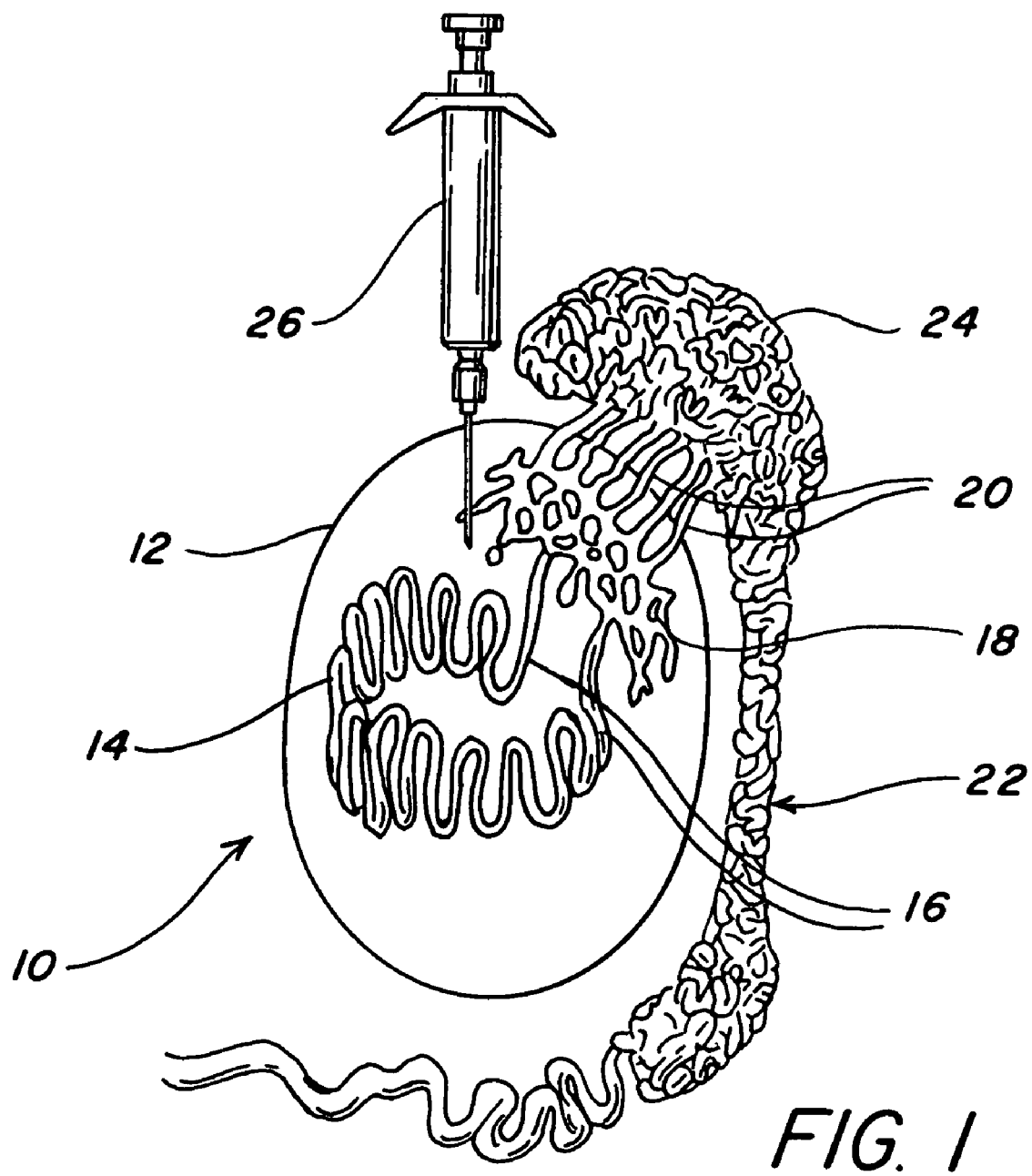
FIG. 1 is a schematic representation of a scrotal testis in cross-section.

As shown in FIG. 1 testis 10 has an oval structure with an outer covering, the fibrous tunica albuginea 12, thickened posteriorly along the epididymal border, where it forms the mediastinum. Fibrous septa extend between the mediastinum and the tunica albuginea to divide each testis into compartments enclosing one or more seminiferous tubules 14. Sperm are produced in the seminiferous tubules 14.

Each seminiferous tubule 14 is lined on its inside by the seminiferous epithelium, which contains two kinds of cells—male germ cells and Sertoli cells. Sperm develop in the seminiferous tubules 14 from less mature cell types. The least mature germinal cells, the spermatogonia, divide to form primary spermatocytes. The primary spermatocytes divide meiotically to form secondary spermatocytes which, in turn, divide mitotically to form spermatids. Spermatids do not divide further, but undergo a complicated metamorphosis in the process of forming sperm. The Sertoli cells nurture the spermatids and secrete a fluid that washes the sperm along the seminiferous tubules 14. The seminiferous tubules 14 are circular in cross-section and regions exist outside the tubules. These interstitial spaces contain blood vessels and Leydig cells which synthesize and secrete testosterone.

The seminiferous tubules 14 form loops, the two terminal portions of which connect with the tubuli recti 16. Sperm, suspended in testicular fluid, leave the seminiferous tubules and enter the tubuli recti 16. These tubules, in turn, join the rete testis 18 which is a network of tubules within the testis 10. At the upper end of the mediastinum, the vessels of the rete testis 18 terminate in the ductuli efferentes 20 which pass through the tunica albuginea 12 and carry the seminal fluid from the testis to the epididymis 22. The passage of sperm through the seminiferous tubules 14, tubuli recti 16, rete testis 18 and ductuli efferentes 20 is passive. The cells lining these ducts have cilia and the beating of these hairlike structures moves the fluid and the suspended sperm through the ducts and into the head of the epididymis 24.

The sperm produced in the seminiferous tubules 14 must undergo a series of changes before they are capable of fertilizing an egg. The journey starts with safe passage through the tubuli recti 16, rete testis 18, ductuli efferentes 20 into the head of the epididymis 24. The epithelium of the tubuli recti 16 and rete testis 18 add fluids which are then reabsorbed by the epithelium in the ductuli efferentes 20. The composition of the fluids in the tubuli recti 16, rete testis 18 and ductuli efferentes 20 is regulated and essential to the provision of viable cells to the epididymis 22 for further processing into mature sperm.

Chemical Sterilant

The chemical sterilant described in U.S. Pat. Nos. 4,937,234 and 5,070,080 is effective at inhibiting spermatogenesis in the seminiferous tubules 14 when injected into the testes 10 of a domesticated or feral mammal having scrotal testes. This includes pets and livestock such as dogs, cats, horses, cattle, pigs and sheep and wild animals such as bears, wolves, deer and so forth.

The chemical sterilant described in the '080 patent is biologically acceptable, effective and non-injurious to the animal. The chemical sterilant is a mineral gluconate salt and an amino acid capable of forming an aqueous solution neutralized to a pH in the range of 6.0 to 7.5. Physiologically acceptable minerals include zinc, calcium, iron, magnesium, manganese and the like and illustrative mineral salts include zinc gluconate.

Zinc gluconate can be neutralized to form a stable aqueous solution with the following amino acids: alanine, valine, isoleucine, proline, glycine, serine, threonine, asparagine, glutamine, lysine, arginine, histidine and mixtures thereof. The solution cannot be formed with cysteine, tyrosine, aspartic acid or glutamic acid and among the basic amino acids, arginine is preferred when the mineral gluconate salt is zinc gluconate.

In neutralizing mineral salts such as zinc gluconate, it is preferred that the mineral salts and the amino acid be present in substantially equimolar amounts. Suitable formulations for use as a chemical sterilant are formed with a molar amount of mineral salt such as zinc gluconate to amino acid such as arginine from about 0.05M:2.0M to about 2.0M:0.05M, preferably from about 0.05M:0.3M to about 0.3M:0.05M and most preferably from about 0.1M:0.2M to about 0.2M:0.1M and neutralized to a pH in the range from about 6.0 to about 8.0, preferably from about 6.5 to about 7.5 and most preferably 7.0. The solution is formed and then sterile filtered into sterile serum vials.

Method of Administration

It is desirable to inject the lowest possible effective amount of chemical sterilant into the testis 10. The volume of sterilant described in U.S. Pat. Nos. 4,937,234 and 5,070,080 needed to effect chemical sterilization depends on the concentration of the active components, the species of the animal being treated and the size of the animal's testes. In U.S. Pat. Nos. 4,937,234 and 5,070,080 the chemical sterilant was injected into the midline of the testis from the side or bottom.

When the sterilant is injected from the side or bottom of the testis, occasionally a small portion of the testis is left intact after treatment. Increasing the dose above the amount expected to be effective is not desirable. It has now been found that injecting 26 the chemical sterilant into the dorsal cranial portion of the testis beside the epididymis 22 effects complete sterilization in substantially all cases with the minimal dose.

The injection into the dorsal cranial portion has an effect on the epithelium of the tubuli recti 16, rete testis 18 and ductus efferentes 20 in addition to the seminiferous tubules 14. If some of the seminiferous tubules 14 in a portion of the testis 10 remain intact, any sperm produced must pass through the above-mentioned transportation system to have any chance at maturing in the epididymis 22 into sperm capable of fertilizing an egg. By affecting the epithelium of the tubuli recti 16, rete testis 18 or ductus efferentes 20, the tubes may not add and remove fluids as is required for the successful development or maintenance of the sperm and there may be no cilia to sweep them along. Hence even if produced in some portion of the testis 10, no viable sperm reach the epididymis 22 so that the sterilization is complete.

When the chemical sterilant consists of an aqueous solution containing 13.1 mg/ml of zinc as zinc gluconate neutralized by 34.8 mg/ml of I-arginine with the pH adjusted to 7.0 with hydrochloric acid, the lowest recommended dose per testicle in a dog three months to ten months of age is based on testicular width measured at its widest part as set out in the following table:

| Dose Corresponding to Testicular Width | |
| --- | --- |
| Range of Testicular Width (mm) | Dose Administered (ml) |
| 10-12 | 0.2 |
| 13-15 | 0.3 |
| 16-18 | 0.5 |
| 19-21 | 0.7 |
| 22-24 | 0.8 |
| 25-27 | 1.0 |

The above table was developed by taking a reference set of data. The testes of a population of puppies were measured and the amount of chemical sterilant necessary to effect sterilization determined clinically. Recommended amounts for more mature dogs and for other species including cats, hogs, cattle, horses and so forth can be clinically determined in the same manner.

The following examples illustrate the invention.

EXAMPLE 1

A beagle puppy weighing 19 lbs at six months of age was injected in each testis with 0.25 ml of a chemical sterilant containing 13.1 mg/ml of zinc as zinc gluconate neutralized by 34.8 mg/ml of I-arginine with the pH adjusted to 7.0 with hydrochloric acid. The injection was into the dorsal cranial portion of the testis as could best be estimated externally.

Figure 3:
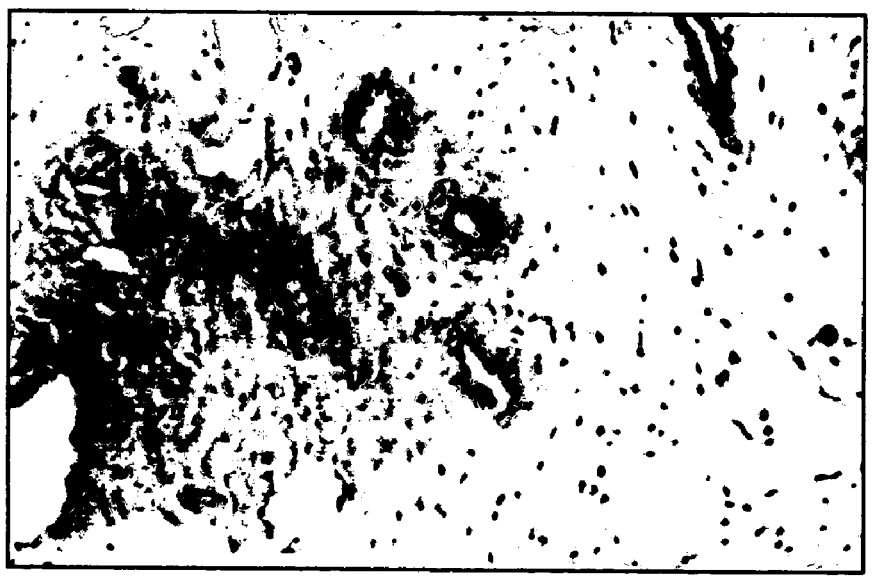

The treated animal was sacrificed at 30 months of age when he weighed 31 lbs. The testes were excised and each weighed 3.5 g. A histological section of the rete testis was taken and a light micrograph of the section at 10× is shown in FIG. 3.

Figure 2:
FIG. 2 is light micrograph showing a histological section of a rete testis from a control dog; and, FIG. 3 is a light micrograph showing a histological section of a rete testis from a dog after treatment with the chemical sterilant described in U.S. Pat. Nos. 4,937,234 and 5,070,080 injected into the dorsal cranial portion of the testis in accordance with the present invention.

A control beagle weighing 18 lbs at six months was housed with the treated animal. This animal was also sacrificed at 30 months. The control dog weighed 30 lbs and each testis weighed 6.8 g. A histological section of the rete testis of the control animal was taken and a light micrograph of the section at 10× is shown in FIG. 2.

In view of the above, it will be seen that the several objects of the invention are achieved and other advantageous results attained. As various changes could be made in the above described method without departing from the scope of the invention, it is intended that all matter contained in the above description shall be interpreted as illustrative and not in a limiting sense.

What is claimed:

1. A method of sterilizing a male animal having scrotal testes with seminiferous tubules flowably connected to a head of an epididymis by tubuli recti, rete testis and ductuli efferentes, said method comprising locating the head of the epididymis in each testis and injecting a chemical sterilant into a dorsal cranial portion of the testis beside the head of the epididymis, said chemical sterilant being an aqueous solution of a mineral gluconate salt and an amino acid capable of forming the solution, said aqueous solution neutralized to a pH in the range of 6.0 to 7.5, said chemical sterilant injected in an amount effective to inhibit spermatogenesis and the transport of sperm through the tubuli recti, rete testis or ductuli efferentes into the head of the epididymis, said animal being a dog or a cat and the mineral gluconate salt being zinc gluconate and the amino acid being I-arginine.

2. The method of claim 1 wherein the dog is a puppy between 3 and 10 months old.

3. The method of claim 1 wherein the aqueous solution is adjusted to about pH 7.0 and contains 13.1 mg/ml zinc as zinc gluconate neutralized by 34.8 mg/ml I-arginine.

* * * * *